United States Patent
Nagamura

(10) Patent No.: US 6,877,151 B2
(45) Date of Patent: Apr. 5, 2005

(54) PHOTOMASK VISUAL INSPECTION SYSTEM

(75) Inventor: Yoshikazu Nagamura, Tokyo (JP)

(73) Assignee: Renesas Technology Corp., Tokyo (JP)

( * ) Notice: Subject to any disclaimer, the term of this patent is extended or adjusted under 35 U.S.C. 154(b) by 242 days.

(21) Appl. No.: 10/214,734

(22) Filed: Aug. 9, 2002

(65) Prior Publication Data

US 2003/0066035 A1 Apr. 3, 2003

(30) Foreign Application Priority Data

Sep. 28, 2001  (JP) ........................................ 2001-303346

(51) Int. Cl.[7] ............................................. G06F 17/50
(52) U.S. Cl. ......................................................... 716/19
(58) Field of Search ..................................... 716/19–21

(56) References Cited

U.S. PATENT DOCUMENTS

2002/0107813 A1 * 8/2002 Kanatani et al. ............... 705/64
2003/0177469 A1 * 9/2003 Suttile et al. .................. 716/21

FOREIGN PATENT DOCUMENTS

JP           11-233582           8/1999

* cited by examiner

*Primary Examiner*—Stacy A. Whitmore
(74) *Attorney, Agent, or Firm*—Burns, Doane, Swecker & Mathis, L.L.P.

(57) ABSTRACT

The coordinate value of the deficient area detected by a wafer inspecting apparatus and the wafer inspecting data are transmitted to a coordinate transforming computer by use of an inspection-data managing computer. The coordinate value detected by the wafer inspection based on the wafer inspecting data and the photomask inspecting data is transformed into the coordinate value on the photomask, to thereby analyze the deficient area of the photomask.

6 Claims, 5 Drawing Sheets

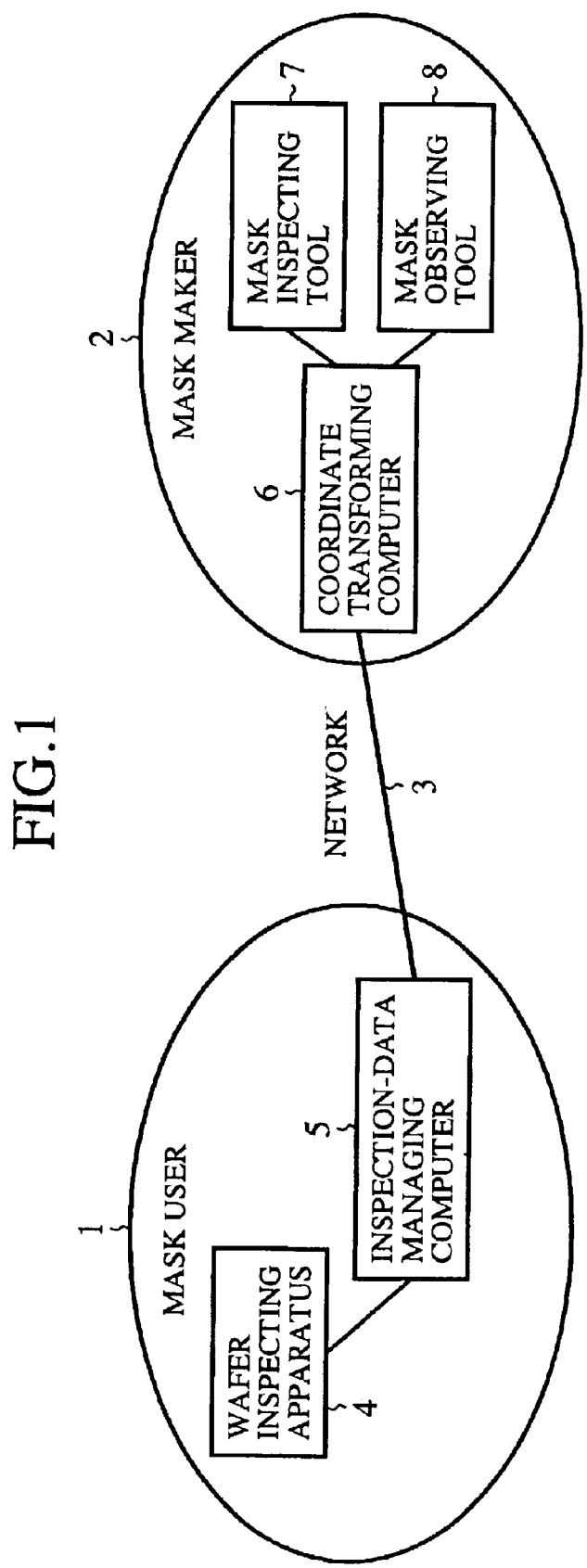

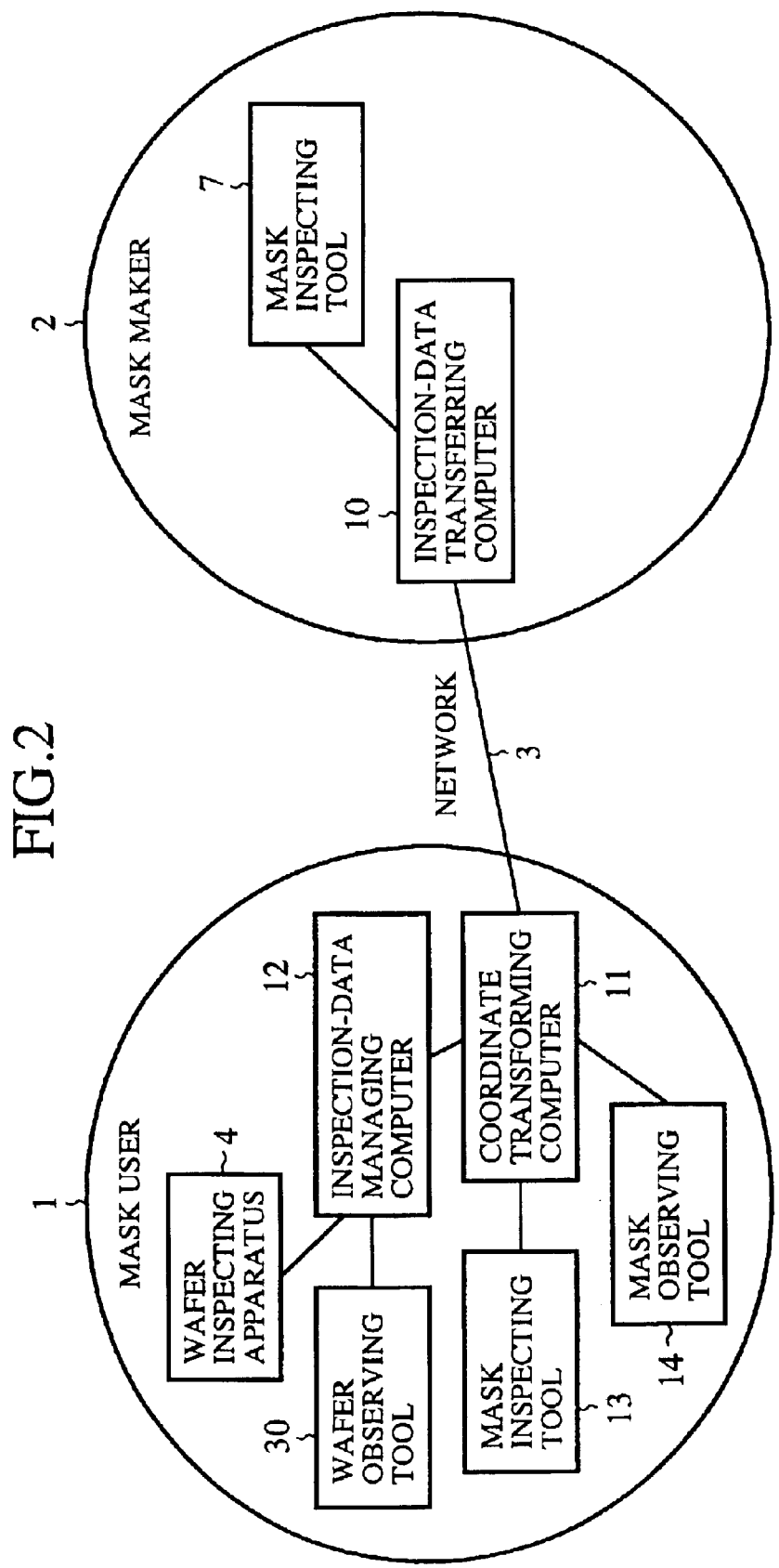

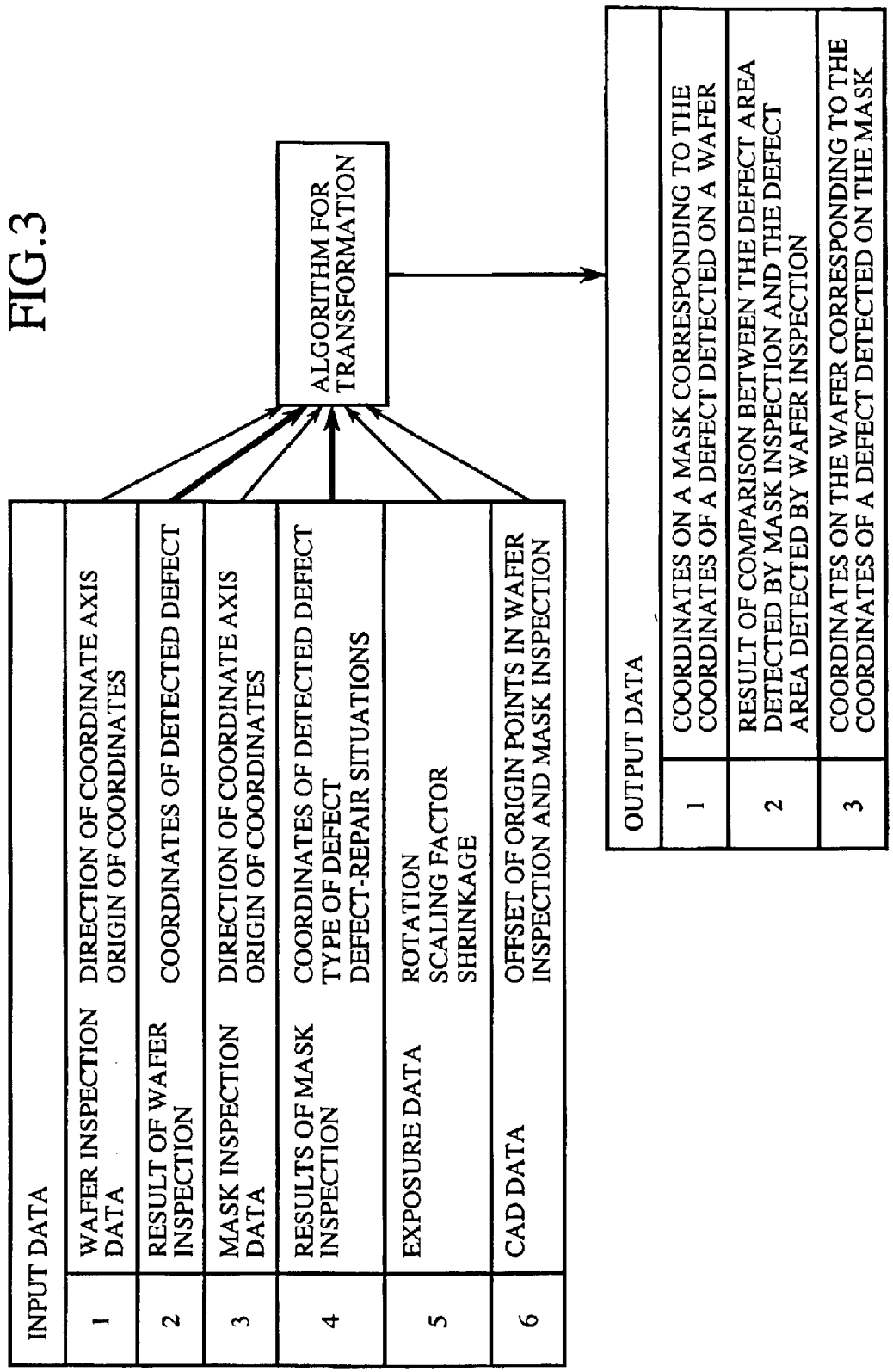

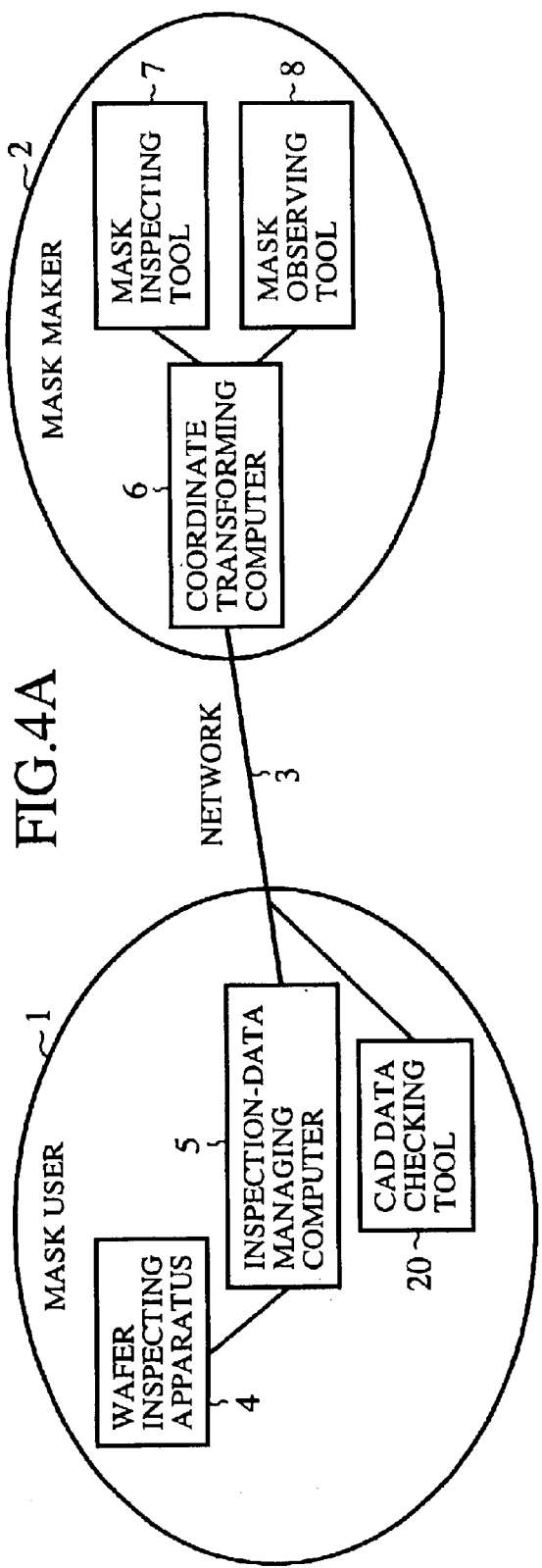
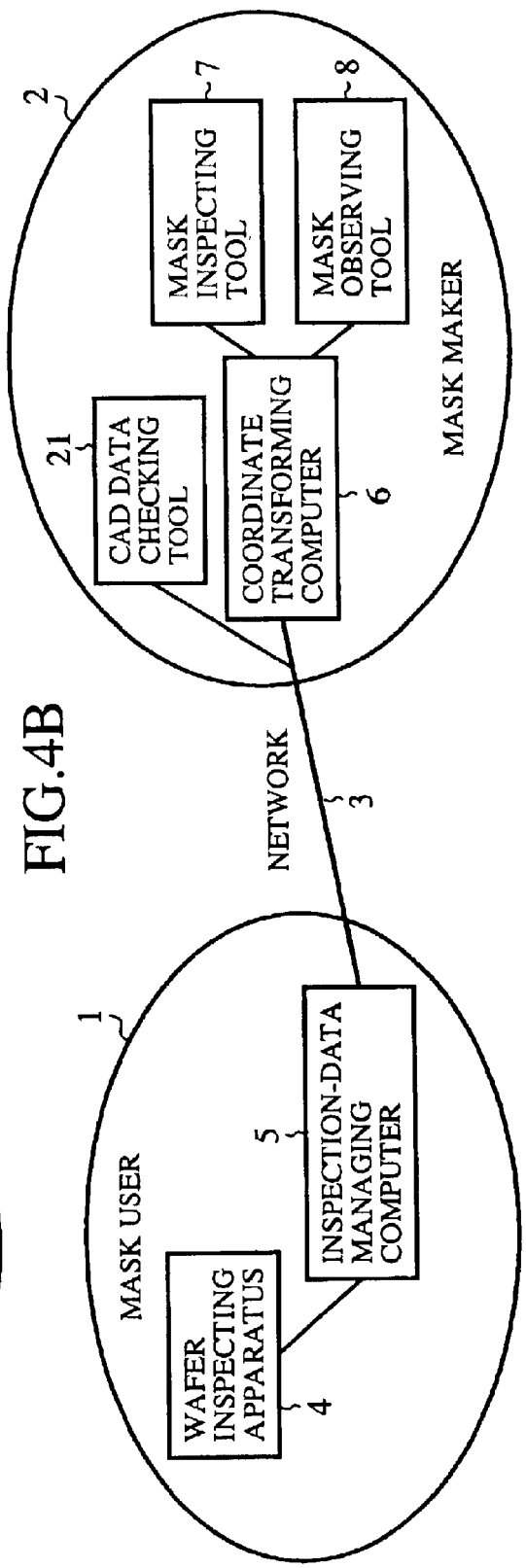
FIG.4A
FIG.4B

PHOTOMASK VISUAL INSPECTION SYSTEM

BACKGROUND OF THE INVENTION

1. Field of the Invention

The present invention relates to a visual inspection system of a photomask used for processing semiconductor products and to a visual inspection method thereof.

2. Description of the Related Art

A photomask (referred to as a mask hereinafter) serves as the master mask of a semiconductor integrated circuit pattern, and is used on an optical aligner such as a stepping projection aligner or stepper. The mask is produced in the following processes: a metallic film such as a chromium oxide film having a shade effect is evaporation-deposited over the surface of a glass substrate having a thickness of several millimeters, and the metallic film thereover is subjected to an etching process, to thereby form an integrated circuit pattern thereof on the surface of the substrate. Conventionally, the mask maker has inspected the mask for an opaque defect that the metallic film remains in excess, a clear defect that by contrast, the metallic film pattern forming the integrated circuit pattern is partially broken, and a particle defect that the mask has a foreign particle on its surfaces. The mask maker has rejected the mask having a defect or a particle that is out of size or number specifications.

Furthermore, in order to complement the mask inspection performed by the mask maker, the semiconductor manufacturer who is the mask user has transferred the circuit pattern of the supplied mask to the wafer, and inspected the wafer to determine whether or not the circuit pattern formed on the wafer can be used. Thus, the semiconductor manufacturer makes an effort to increase the yields of their semiconductor products. When by the wafer inspection carried out by the mask user, the defects are detected in the same coordinate position among a plurality of chips, that is, when the common defects among a plurality of chips are detected, there is a high probability that the mask has a deficiency such as a defect. In this case, the mask user finds out a position on the mask in which the defect is located from a coordinate value which represents a position on the wafer in which the common defect detected by the wafer inspection is located, to thereby analyze the causes of the deficiency. At that time, the mask user's wafer inspection conditions have been different from the mask maker's mask inspection conditions. That is, the conditions of setting the direction in which the mask pattern is disposed, the inspection area, the origin of coordinates, and the axes of coordinates, used in the mask inspection previously performed by the mask maker have been different from the ones used in the wafer inspection. Therefore, it has been necessary to transform or apply the data such as the coordinate value or the like which represents the defect area detected by the wafer inspection into the data used in the mask inspection.

FIG. 5 is an explanatory view showing one example illustrating the relation between the pattern located on the wafer and the one located on the mask, and the relation between the origin of coordinates used in the wafer inspection and the origin of coordinates used in the mask inspection. FIG. 5 is also an explanatory view showing one example describing the method of transforming the coordinate value used in the wafer inspection into the one used in the mask inspection. In the figure, "a" designates a pattern located on the wafer, and represented in the coordinate system used in the wafer inspection; "aO" designates the origin of the rectangular coordinates consisting of x-and y-axes included in the wafer inspecting data, which are used for showing the position of the pattern "a" located on the wafer; "b" designates a pattern located on the mask, shown in the coordinate system used in the mask inspection; and "bO" designates the origin of the rectangular coordinate system consisting of x-and y-axes included in the mask inspecting data, which are used for showing the position of the pattern "b" located on the mask. In the figure, the left lower corner position of the pattern "a" located on the wafer is defined by the origin of the coordinate system "aO", and the left lower corner position of the pattern "b" located on the mask is defined by the origin of the coordinate system "bO". The pattern "a" located on the wafer and the pattern "b" located on the mask are disposed in the relation in which the pattern "a" is obtained by mirror-reversing the pattern "b" with an optional axis extended in the y-axis direction as a center. Herein, the pattern obtained by scaling down the pattern "b" located on the mask is shown as the pattern "a" located on the wafer.

The inspection and observation of the mask are performed from the side of the mask substrate (glass substrate) on which the pattern (formed in the metal film such as chromium oxide) is located (the pattern-surface side). On the other hand, the transferring (or exposure) of the pattern onto the wafer is performed by irradiating the photoresist formed over the wafer with light from the side of the mask substrate on which the pattern is not located (the glass-surface side). For this reason, the image obtained by mirror-reversing the image located on the pattern-surface side of the mask is formed on the wafer. That is, the image formed on the wafer is the image seen from the glass-surface side of the mask. Therefore, in order to observe a defective area detected by the wafer inspection on the mask, it is necessary to transform a coordinate value representing the position on the wafer into a coordinate value representing a position on the mask. This coordinate transformation converts the coordinate value representing the position of the defect area detected by the wafer inspection into the coordinate value on the mask. The coordinate value thus obtained on the mask is used for the mask observation, and the area in which the defect is located is determined, to thereby analyze the deficiency.

Conventionally, the transformation of the coordinate value used in the wafer inspection into the coordinate value used in the mask inspection has been carried out as mentioned above. However, with a recent increase in the degree of integration of semiconductor products, requirements against defective points and foreign particles located on the mask have been increasingly stricter. Therefore, the mask inspection carried out by the mask maker cannot achieve the sensitivity required for effectively dealing with the defective portion and foreign particle. Moreover, the coordinate value used in the mask inspection does not have direct compatibility with the coordinate value used in the wafer inspection carried out by the mask user so as to complement the mask inspection done by the mask maker. Therefore, it is necessary to transform the coordinate value of the deficient area detected on the wafer in order to observe the mask for analyzing the cause of the deficiency. In addition, the inspection conditions of the mask inspection done by the mask maker vary from one mask maker to another in the position from which the inspection begins and in the direction in which the inspection proceeds, on the circuit pattern formed on the mask. For this reason, the coordinate value data used in the mask inspection and the coordinate value data obtained in the wafer inspection done by the mask user sometimes stand in the relationship in which the former is rotated with respect to the latter with the coordinate values being of opposite sign to each other. It is sometimes necessary to flip the coordinate value 90 or 180 degrees in the coordinate transformation mutually done between the coordinate values. The data showing the results of the mask inspection varies from one mask maker to another in the requirements or specifications. There has been a drawback that it is necessary to transform the coordinate value of the defect area detected by the wafer inspection by use of the transforming method compatible to the inspection performed by each mask maker.

Additionally, because the mask user performs the wafer inspection, and the mask maker performs the mask inspection, there have been the following drawbacks. The data such as the origins of coordinates or the coordinate axes used in each inspection can be misinformed. The deficiency of the mask cannot be analyzed because the coordinate transformation is not properly done due to misunderstanding the inspection data. The analysis of the deficiency takes much time.

Moreover, a wasteful time is taken because miscalculation easily occurs due to the complex transformation of the coordinate value. As a result, there has been a drawback that the production of semiconductor products is delayed because of delayed deliveries of the mask for producing wafers, and thereby serious damage can occur.

SUMMARY OF THE INVENTION

The present invention has been accomplished to solve the above-mentioned drawbacks. An object of the present invention is to provide a photomask visual inspection system and a method of visually inspecting a photomask that can analyze the deficiency of a mask with efficiency by means of transmitting the inspection data of the mask user or the mask maker over a network.

According to a first aspect of the present invention, a photomask visual inspection system is characterized in that a photomask user which processes a wafer by use of the photomask includes: a wafer inspecting means for inspecting the processed wafer; and an inspection-data managing means that transmits a coordinate value which represents the position of a deficient area within a pattern located on the wafer detected by the wafer inspecting means and the wafer inspecting data used in the wafer inspecting means to the photomask maker, wherein the photomask visual inspection system has the photomask maker observe the deficient area within the photomask based on the transmitted coordinate value and wafer inspecting data.

Thus, this system allows to quickly analyze the causes of the deficiency of the photomask and adopt rapidly these remedies, thereby repairing the photomask speedily.

According to a second aspect of the present invention, a photomask visual inspection system is characterized in that a photomask maker which produces the photomask includes: a photomask inspecting means for inspecting the produced photomask; a coordinate transforming means which receives a coordinate value, which represents the position of a deficient area within a pattern located on the wafer detected by a wafer inspection carried out by the photomask user, and the wafer inspecting data used in the wafer inspection, and which transforms the received coordinate value into a coordinate value which represents the position of a deficient area within a pattern located on the photomask, based on the photomask inspecting data used in the photomask inspecting means and the received wafer inspecting data; and a photomask observing means for observing the photomask, based on the coordinate value transformed by the coordinate transforming means.

Thus, this system allows to quickly analyze the causes of the deficiency of the photomask and adopt rapidly these remedies, thereby repairing the photomask speedily.

According to a third aspect of the present invention, a photomask visual inspection system is characterized in that a photomask maker which produces a photomask includes: a photomask inspecting means for inspecting the produced photomask; and an inspection-data transferring means that transmits a coordinate value, which represents the position of a deficient area within the pattern located on the photomask detected by the photomask inspecting means, and the photomask inspecting data used in the photomask inspecting means to the photomask user, wherein the photomask visual inspection system has the photomask user inspect the photomask by use of the transmitted coordinate value and photomask inspecting data.

Thus, this system allows to quickly analyze the causes of the deficiency of the photomask and adopt rapidly these remedies, thereby repairing the photomask speedily.

According to a fourth aspect of the present invention, a photomask visual inspection system is characterized in that a photomask user which processes a wafer by use of the photomask includes: a wafer inspecting means for inspecting the processed wafer; an inspection-data managing means for managing the coordinate value representing the position of a deficient area within a pattern located on the wafer detected by the wafer inspecting means and the wafer inspecting data used in the wafer inspecting means; and a coordinate transforming means that receives the coordinate value representing the position of the deficient area within the pattern located on the photomask detected by the photomask inspection performed by the photomask maker and the photomask inspecting data used in the photomask inspection, obtains the coordinate value and wafer inspecting data managed by the inspection-data managing means, performs a coordinate transformation based on the received photomask inspecting data and the obtained wafer inspecting data, and compares and/or collates the coordinate value detected by the wafer inspecting means with the coordinate value detected by the photomask inspection.

Thus, this system allows to quickly analyze the causes of the deficiency of the photomask and adopt rapidly these remedies, thereby repairing the photomask speedily.

BRIEF DESCRIPTION OF THE DRAWINGS

FIG. 1 is a configuration diagram showing the photomask visual inspection system according to Embodiment 1 of the present invention;

FIG. 2 is a configuration diagram showing the photomask visual inspection system according to Embodiment 2 of the present invention;

FIG. 3 is an explanatory diagram describing the contents of the control carried out by the computer used for the coordinate transformation according to Embodiment 3 of the present invention;

FIG. 4A and FIG. 4B are configuration diagrams showing the photomask visual inspection system according to Embodiment 4 of the present invention.

DETAILED DESCRIPTION OF THE PREFERRED EMBODIMENTS

Figure 5:
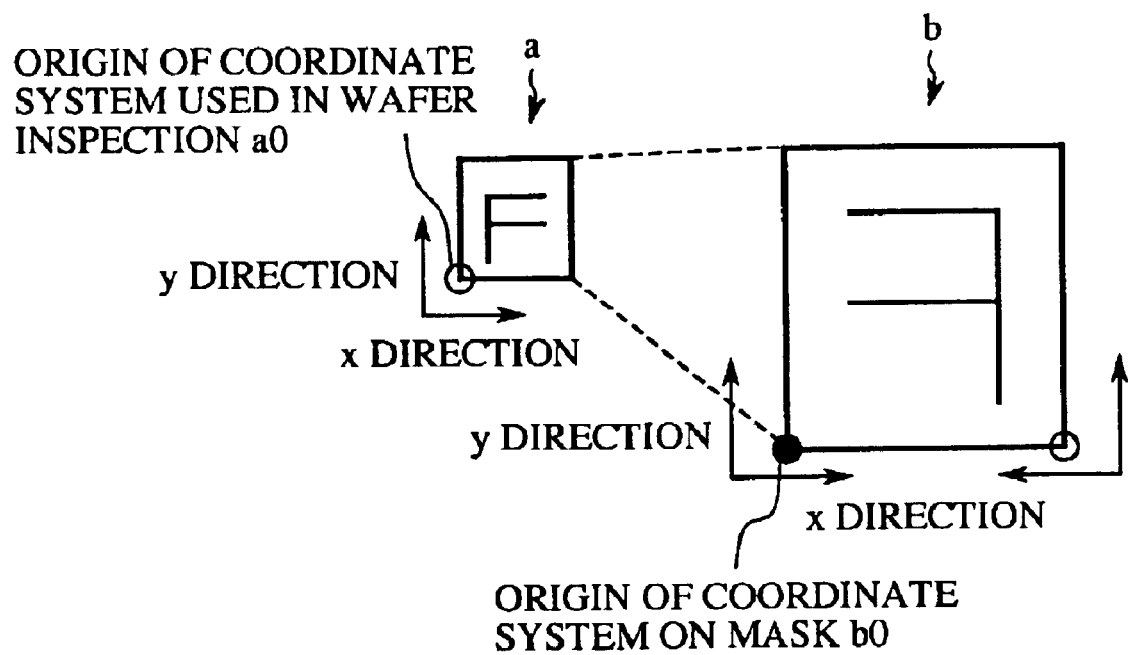
FIG. 5 is an explanatory view describing the conventional method of transforming the coordinate value used in the wafer inspection into the coordinate value used in the mask inspection.

An embodiment of the present invention will be described below.

Embodiment 1

FIG. 1 is a configuration diagram showing the photomask visual inspection system according to an embodiment 1 of the present invention. A photomask is referred to as a mask hereinafter. Referring to the figure, reference numeral 1 denotes a mask user who is a semiconductor manufacturer (photomask user); numeral 2 denotes a mask maker who produces the mask (photomask maker); and numeral 3 denotes a network that is a communication network such as the Internet or the like. Numeral 4 denotes a wafer inspecting apparatus (wafer inspecting means) that is provided by the mask user 1, detects a deficient area within the pattern located on the wafer, and outputs the coordinate value representing the position thereof and the wafer inspecting data. The wafer inspecting data used in the wafer inspecting apparatus 4 consists of the following data: the pattern arrangement recorded when inspecting the wafer, the inspection area within the wafer, and the axes and origin of coordinates used in the inspection.

Numeral 5 denotes an inspection-data managing computer (inspection-data managing means) that is provided by the mask user 1, and manages the coordinate value representing the position of the deficient area and the wafer inspecting data output from the wafer inspecting apparatus 4.

Numeral 6 denotes a coordinate transforming computer (coordinate transforming means) that is provided by the mask maker 2, and transforms the coordinate value representing the position of the deficient area of the pattern located on the wafer output from the wafer inspecting apparatus 4 into the coordinate value that can be used by a mask observing tool 8 described later. Numeral 7 denotes a mask inspecting tool (photomask inspecting means) that is provided by the mask maker 2, is connected to the coordinate transforming computer 6, detects the defect area and the foreign particle on the mask, and outputs the data such as the coordinate value representing the position in which the defect or the like is detected and the image, and the mask inspecting data. The mask inspecting data (photomask inspecting data) used in the mask inspecting tool 7 consists of the following data: the inspection direction within the mask, the inspection area within the mask, and the axes and origin of coordinates used for the mask inspection.

Numeral 8 denotes a mask observing tool (photomask observing means) such as a scanning electron microscope (referred to as a SEM hereinafter) which is provided by the mask maker 2, is connected to the coordinate transforming computer 6, and observes the mask by use of the coordinate value representing the position of the deficient area within the pattern located on the wafer which is detected by the wafer inspecting apparatus 4 and transformed by the coordinate transforming computer 6 or the coordinate value representing the position of the deficient area within the pattern located on the mask output from the mask inspecting tool 7. The inspection-data managing computer 5 of the mask user 1 and the coordinate transforming computer 6 of the mask maker 2 are connected to each other through the network 3 and arranged to perform the data communication.

The operation will next be described as below.

The mask maker 2 produces a mask requested by the mask user 1, inspects the mask by use of the mask inspecting tool 7, repairs a deficient area on the mask when the deficient area is detected within the pattern located on the mask by this inspection, stores the coordinate value representing the repaired area in a predetermined storage means (not shown), and delivers the mask that met the predetermined specifications by being repaired to the mask user 1. The mask user 1 receives the mask, actually produces a semiconductor wafer by use of this mask, and inspects to confirm whether or not there is a defect or foreign particle within the circuit pattern formed on the wafer by use of the wafer inspecting apparatus 4. The data showing the result of this inspection is input to the inspection-data managing computer 5 together with the wafer inspecting data. Thus, the management such as the storage and transmission to outside of this wafer inspecting data is performed.

When a common defect that is found in the same position in each of a plurality of chips formed on the wafer is detected by the wafer inspection, the probability that the mask has a deficiency that is the cause of the defect on its surface is higher than the probability that a deficiency came up on the wafer in the wafer-processing step or process. Therefore, when a common defect is detected by the wafer inspection, a detailed observation is carried out on the mask.

When a defect or foreign particle is found on the wafer from the result of the inspection carried out by use of the wafer inspecting apparatus 4, the inspection-data managing computer 5 transmits the coordinate value representing the position where the deficiency is found, together with the wafer inspecting data to the coordinate transforming computer 6 of the mask maker 2 through the network 3. The coordinate transforming computer 6 has coordinate-transforming software used for transforming the coordinate value, performs the transforming process based on the relation between the wafer inspecting data and the mask inspecting data by use of the software, and transforms the coordinate value representing the position of the deficient area within the pattern located on the wafer detected by the wafer inspection into the coordinate value representing the position on the mask, which can be used by the mask observing tool 8 or the mask inspecting tool 7.

The coordinate value representing the position of the deficient area within the pattern located on the wafer, which is transformed by the coordinate transforming computer 6, is transmitted to the mask inspecting tool 7 or the mask observing tool 8 such as the SEM, to thereby perform the inspection and observation. The mask observing tool 8 determines the place within the mask to be observed from this coordinate value, and carries out a detailed observation thereon. The mask maker 2 analyzes the cause of the deficiency from the results of this observation, and thereby solves the deficiency.

Moreover, a comparison (or collation) of the coordinate value representing the position of the deficient area within the pattern located on the wafer, transformed by the coordinate transforming computer 6, and the result of the mask inspection (the coordinate value representing the position of the deficient area within the pattern located on the mask detected by the mask inspection, the mask inspecting data, and the like) carried out before the mask is delivered, makes it possible to analyze the deficiency of the mask inspection and the mask repair performed before the delivery of the mask (determine whether or not the repair of the defect is proper). The analysis of the deficiency is performed as follows: the coordinate value representing the position of the area of the deficiency on the wafer detected by the wafer inspection is transformed into the coordinate value on the mask by the coordinate transforming computer 6; the obtained coordinate value on the mask is compared (or collated) with the coordinate value representing the position of the deficient area on the mask detected by the mask inspection before the delivery of the mask which is stored in a predetermined storage means (not shown); and the mask is observed on the coordinate values coinciding with each other by use of the mask observing tool 8, to thereby analyze the deficiency. When the deficient area recorded in the result of the mask inspection done before the delivery of the mask, that is, the coordinate value representing the position of the repaired area coincides with the coordinate value representing the position of the deficient area on the wafer detected in the wafer inspection, it is found that the repair of the deficient area carried out before the delivery of the mask has not been properly performed. It is considered that for this reason the deficiency came up in the circuit pattern formed on the wafer. Thus, the analysis of the deficiency can be performed, to thereby determine what caused the defect detected on the wafer.

As mentioned above, according to the embodiment 1, the photomask inspection system is arranged such that the coordinate value representing the position of the defect area within the pattern located on the wafer detected by the wafer inspecting apparatus 4, is transmitted over the network 3, and the coordinate value representing the position of the defect area within the pattern located on the wafer is transformed into the coordinate value that can be used for the mask observation. As a result, the analysis of the deficiency located on the mask can be performed in real time concerning the deficiency detected on the wafer, the deficiency located on the mask can be quickly eliminated, and the delivery times of semiconductor products can be observed, to thereby prevent the occurrence of delayed deliveries having an influence on the business.

Embodiment 2

FIG. 2 is a configuration diagram showing the photomask visual inspection system according to an embodiment 2 of the present invention. The same (or corresponding) components as those described in the embodiment 1 are designated by the same numerals, and the detailed description will be omitted. The wafer inspecting data and mask inspecting data used in the description of the embodiment 2 are similar to those described in the embodiment 1, and the detailed description will be omitted also. Referring to the figure, reference numeral 10 denotes an inspection-data transferring computer (inspection-data transferring means) provided by the mask maker 2, which transfers the coordinate value representing the position of the deficient area within the pattern located on the mask, detected by the mask inspection performed by the mask inspecting tool 7 before the delivery of the mask and the mask inspecting data used in the mask inspecting tool 7, to a coordinate transforming computer 11 that is described later.

Numeral 11 denotes a coordinate transforming computer (coordinate transforming means) provided by the mask user 1, which transforms the coordinate values showing the position of the deficient area detected by the mask inspection and detected by the wafer inspection into the predetermined coordinate values, based on the input mask inspecting data and wafer inspecting data, respectively. Numeral 12 denotes an inspection-data managing computer (inspection data managing means) provided by the mask user 1, which manages the coordinate value representing the position of the deficient area of the pattern located on the wafer and the wafer inspecting data, output from the wafer inspecting apparatus 4. Numeral 13 denotes a mask inspecting tool provided by the mask user 1, which detects the deficient area located on the delivered mask, and outputs the coordinate value and image showing the position of the deficient area within the pattern located on the mask by use of a coordinate system other than the coordinate system used in the mask inspecting tool 7 provided by the mask maker 2. Numeral 14 denotes a mask observing tool (photomask observing means) provided by the mask user 1, which observes the delivered mask by use of a coordinate system other than the coordinate system used in the mask inspecting tool 7 provided by the mask maker 2. Numeral 30 denotes a wafer observing tool provided by the mask user 1, which observes the deficient area within the pattern located on the wafer by use of the coordinate value representing the position of the deficient area within the pattern located on the wafer and wafer inspecting data output by the wafer inspecting apparatus 4. Additionally, the network 3 connecting the mask user 1 and the mask maker 2 to enable the communication therebetween is connected with the inspection-data transferring computer 10 and the coordinate transforming computer 11.

The operation will next be described below.

The mask maker 2 inspects the produced mask by use of the mask inspecting tool 7, and delivers the mask to the mask user 1. The result (the coordinate value representing the position in which the deficiency within the pattern located on the mask is detected and the mask inspecting data) of the mask inspection carried out at the time is input to the inspection-data transferring computer 10 by the mask inspecting tool 7. For instance, when delivering the mask to the mask user 1, the result of the inspection is transmitted to the coordinate transforming computer 11 provided by the mask user 1, by the inspection-data transferring computer 10 through the network 3.

The mask user 1 receives the mask delivered by the mask maker 2, and produces a wafer by use of the mask. The wafer is subjected to an inspection done by use of the wafer inspecting apparatus 4. The coordinate value representing the position of the detected deficient area and the wafer inspecting data are input to the inspection-data managing computer 12 and managed therein. Subsequently, as required, the inspection-data managing computer 12 inputs the coordinate value representing the position of the deficient area within the pattern located on the wafer and wafer inspecting data managed by itself to the coordinate transforming computer 11.

The coordinate transforming computer 11 performs the basically similar transformation to the processing operation carried out by the coordinate transforming computer 6, described in the embodiment 1. That is, the transformation is done, by use of the coordinate transforming software provided in the coordinate transforming computer 11, based on the coordinate value representing the position of the deficient area within the pattern located on the wafer detected by the wafer inspecting apparatus 4, the wafer inspecting data used the wafer inspection, the coordinate value representing the position of the deficient area within the pattern located on the mask detected by the mask inspecting tool 7, transmitted from the inspection-data transferring computer 10 over or by way of the network 3, and the mask inspecting data used in the mask inspection. Thus, the coordinate transforming computer 11 transforms the coordinate value representing the position of the deficient area within the pattern located on the mask output from the wafer inspecting apparatus 4 into the coordinate value in the coordinate system used in the mask inspecting tool 7.

The coordinate transforming computer 11 compares and/or collates the above transformed coordinate value with the coordinate value of the deficient area detected by the mask inspecting tool 7, that is, the coordinate value of the area repaired by the mask maker 2 before delivering the mask. As a result, when these coordinate values coincide with each other, it is known that the repair of the deficient area of the mask done before the delivery of the mask has been not properly carried out. Therefore, it can be considered that the deficiency came up within the circuit pattern formed on the wafer for this reason. Thus, the mask user 1 analyzes the cause of the deficiency detected on the wafer, and informs the mask maker 2 of the deficient area within the mask and the result of the analysis, to thereby repair the deficient area within the mask.

In the above description, the coordinate value representing the position of the deficient area within the pattern located on the wafer detected by the wafer inspecting apparatus 4 is transformed into the coordinate value corresponding to the mask inspecting data stored in the mask inspecting tool 7. However, the coordinate transforming computer 11 may transform the coordinate value representing the position of the deficient area within the pattern located on the mask detected by the mask inspecting tool 7 into the coordinate value corresponding to the wafer inspecting data stored in the wafer inspecting apparatus 4, to thereby compare or collate the transformed coordinate value with the coordinate value representing the position of the deficient area within the pattern located on the wafer detected by the wafer inspecting apparatus 4.

Moreover, the coordinate transforming computer 11 transforms the coordinate value of the deficient area detected by the wafer inspecting apparatus 4 into the coordinate value used in the mask observing tool 14 or the mask inspecting tool 13. This transforming processing transforms the coordinate value representing the position of the deficient area within the pattern located on the wafer detected by the wafer inspecting apparatus 4 into the coordinate value in the coordinate system used in the mask observing tool 14 or the mask inspecting tool 13, based on the wafer inspecting data acquired from the inspection-data managing computer 12 and the mask inspecting data acquired from the mask inspecting tool 13 or the mask observing tool 14. The mask is inspected or observed by use of this transformed coordinate value, and if necessary, by use of the mask inspecting tool 13 or the mask observing tool 14, to thereby investigate the deficient area. Thus, the mask user 1 determines whether or not the causes of the deficiency detected by the wafer inspection belongings to the mask, and collects the required data, to thereby request the repair of the deficient area within the mask to the mask maker 2.

The coordinate transforming computer 11 can also transform the coordinate value of the deficient area, which is detected by the mask inspecting tool 7 and transmitted from the inspection-data transferring computer 10, into the coordinate value that can be used in the mask observing tool 14, the mask inspecting tool 13, the wafer inspecting apparatus 4 or the wafer observing tool 30. When the coordinate transforming computer 11 performs such transformation, the mask user 1 can inspect or observe the deficient area by himself, detected by the mask inspection performed by the mask maker 2 before the delivery of the wafer, can actually inspect the delivered mask, and can identify the change of the pattern in the deficient area detected by the mask inspection. Additionally, the mask user 1 can analyze the cause of the deficiency by means of further transforming the coordinate value representing the area of the deficiency detected by the mask inspecting tool 7 which is found to coincide with the area of the deficiency detected by the above-described wafer inspecting apparatus 4 by comparing or collating these areas into the coordinate value that can be used in the mask inspecting tool 13 or the mask observing tool 14, using the mask inspecting tool 13 or the mask observing tool 14, and inspecting or observing the mask by himself. When the mask inspecting data used in the mask inspecting tool 7 provided by the mask maker 2 and the mask inspecting data used in the mask inspecting tool 13 or the mask observing tool 14 provided by the mask user 1 are the same, that is, when the coordinate value is handled by means of using the same coordinate system, the mask can be observed or inspected by use of the coordinate value of the deficient area of the pattern located on the mask output from the mask inspecting tool 7, and the mask inspecting tool 13 or the mask observing tool 14 without transforming the coordinate value by use of the coordinate transforming computer 11.

As mentioned above, according to the embodiment 2, the photomask inspection system is arranged such that the coordinate value representing the position of the deficient area within the pattern located on the wafer detected by the wafer inspecting apparatus 4 is compared and/or collated with the coordinate value representing the deficient area within the pattern located on the mask detected by the mask inspection done by use of the mask inspecting tool 7 before the delivery of the mask. As a result, it is easy to determine whether or not the deficient area detected by the wafer inspection corresponds to the area in which the defect located on the mask is repaired before the delivery of the mask.

In addition, the photomask inspection system is arranged such that the wafer inspection is done by use of the wafer inspecting apparatus 4 of the mask user 1, and the coordinate value of the deficient area detected thereby is coordinate-transformed by use of the coordinate transforming computer 11, to thereby observe the mask by use of the mask observing tool 14 or inspect the mask by use of the mask inspecting tool 13. As a result, the mask user 1 can observe the deficient area located on the mask, and analyze the deficiency, to thereby easily and quickly analyze the caused of the deficiency on the mask.

Furthermore, the photomask inspection system is arranged such that when delivering the mask, the mask maker 2 transmits the coordinate value representing the deficient area within the mask detected by the mask inspecting tool 7 from the inspection-data transferring computer 10 to the coordinate transforming computer 11. As a result, the mask user 1 can more effectively adopt remedies against the deficiency on the wafer when detecting the deficiency by the wafer inspection.

Embodiment 3

FIG. 3 is an explanatory diagram describing the contents of the software for coordinate transformation used in the coordinate transforming computer 6 described in the embodiment 1 or in the coordinate transforming computer 11 described in the embodiment 2, that is, the contents of the control performed by the coordinate transforming computer 6 and the coordinate transforming computer 11. The contents of the control are broadly classified into the following processes.

(1) The coordinates on the wafer are mirror reversed.
(2) The offset caused in the positional relationship between the origin of the coordinate used in the wafer inspection and the origin of the coordinate used in the mask inspection or in the mask observation is determined following the instruction given in the following i), by incorporating the data obtained from the processing of which the contents are illustrated in ii) and iii).

i) The corresponding position on the mask is determined with respect to the position of the origin of the coordinate on the wafer.

ii) The rotation and scaling factor in the transfer/exposure when forming the pattern on the wafer are determined.
iii) The shrinkage of the pattern located on the mask is determined.

The order where the processes of which contents are illustrated in i)–iii) are carried out is not limited to the order described above.

(3) The coordinate value representing the deficient area detected by the wafer inspection is transformed by incorporating the offset of the origin of the coordinates, into the corresponding coordinate value in the coordinate system used in the mask inspection.

(4) A comparison and/or collation between the coordinate value detected by the wafer inspection and transformed in the process (3) and the coordinate value representing the deficient area detected when inspecting the mask is performed.

(5) The coordinate value representing the deficient area detected by the mask inspection is transformed by incorporating the offset of the origin of the coordinates, into the corresponding coordinate value in the coordinate system used in the wafer inspecting apparatus and the wafer observing tool.

In the process (1), "Wafer inspecting data (Direction of coordinate axis and Origin of coordinates)" of Input data 1 shown in FIG. 3 and "Result of wafer inspection (Result of detection by wafer inspection)" of Input data 2 shown in FIG. 3 are input, and the mirror reversing process is performed with respect to this input data. In the process (2), "Mask inspecting data (Direction of coordinate axis and Origin of coordinates)" of Input data 3 and "Exposure data (Rotation, Scaling factor, and Shrinkage)" of Input data 5 shown in FIG. 3 are input, and the offset of the origin of coordinates used in the mask inspection is determined. In the process (3), the coordinate transformation is done with respect to "Result of wafer inspection" of Input data 2 in consideration of the offset of the origin of coordinates, and "Coordinate value on mask corresponding to coordinate value detected by wafer inspection" of Output data 1 is output. In the process (4), a comparison and/or collation between "Result of mask inspection (Coordinate value of detected defect, Type of defect, and Defect-repair situations)" of Input data 4 shown in FIG. 3 and the coordinate value obtained in the process (3) determines whether or not these coordinate values are the same to each other, and the result is output as "Result of comparison and/or collation between the area where a defect is detected by mask inspection and the area where a defect is detected by wafer inspection" of Output data 2 shown in FIG. 3. Additionally, in the process (5), a coordinate transformation is done with respect to "Results of mask inspection" of Input data 4 shown in FIG. 3 in consideration of the offset of the origin of coordinates obtained in the process (1), and thereby "Coordinate value on a wafer corresponding to a transformed coordinate value detected by mask inspection" of Output data 3 is obtained.

As mentioned above, according to the embodiment 3, the photomask inspection system is arranged such that the coordinate value representing the position of the deficient area within the pattern located on the wafer detected by the wafer inspection is transformed into the coordinate value on the mask used in the mask inspection or the mask observation, based on the wafer inspecting data, the mask inspecting data, and the exposure data. As a result, the deficient area within the pattern located on the wafer detected by the wafer inspection can be precisely transformed into the coordinate value on the mask with efficiency, and the deficiency of the mask can be quickly analyzed and solved, to thereby improve the yield of the semiconductor products. Moreover, the photomask inspection system is arranged such that the coordinate value representing the position of the deficient area within the pattern located on the mask detected by the mask inspection is transformed into the coordinate value on the wafer used in the wafer inspection or the wafer observation based on the mask inspecting data and the exposure data. As a result, the deficiency on the wafer caused by the deficiency within the pattern located on the mask can be quickly analyzed.

Embodiment 4

FIG. 4A and FIG. 4B are configuration diagrams showing the photomask visual inspection system according to an embodiment 4. The same (or corresponding) parts as the ones in FIG. 1 described in Embodiment 1 are designated by the similar numerals, and the description is omitted. Referring to FIG. 4A, reference numeral 20 denotes a CAD data checking tool (CAD data checking means) checking the data of the CAD device (not shown) designing the pattern located on the mask, provided by the mask user 1. Referring to FIG. 4B, reference numeral 21 denotes a CAD data checking tool (CAD data checking means) checking the data of the CAD device (not shown) designing the pattern located on the mask, provided by the mask maker 2.

The operation will next be described below.

The photomask visual inspection systems shown in FIG. 4A and FIG. 4B operate similarly to the photomask visual inspection system described in the embodiment 1 except that the coordinate transformation is done by means of determining the amount of offset from the CAD data having designed the mask by use of the coordinate transforming computer 6. The description is omitted.

The photomask visual inspection system shown in FIG. 4A comprises a CAD data checking tool 20 provided by the mask user 1 and connects this tool with the network 3. The CAD data checking tool 20 has a software program that extracts the coordinate data constituting CAD data. The CAD data checking tool 20 extracts coordinate data showing the origin used when designing the CAD data of the mask, for instance, from the CAD data of the mask. The amount of offset between the origin of coordinates included in the wafer inspecting data that is described in the embodiment 3 and the origin of coordinates included in the mask inspecting data is determined by means of predetermined calculation by use of the data showing the origin of coordinates.

The coordinate transforming computer 6 calculates the difference between the origin of coordinates included in the CAD data and the origin of coordinates included in the wafer inspecting data. Moreover, the coordinate transforming computer 6 calculates the difference between the origin of coordinates included in the CAD data and the origin of coordinates included in the mask inspecting data. The difference between the origin of coordinates included in the wafer inspecting data and the origin of coordinates included in the mask inspecting data can be shown as an absolute amount by use of thus calculated value with respect to the origin of coordinates included in the CAD data. This absolute amount is determined by calculation, and the predetermined data processing is done with the obtained absolute amount as the amount of offset, to thereby perform the coordinate transformation processing.

The photomask visual inspection system shown in FIG. 4B extracts the origin of coordinates used when designing the CAD data of the mask, for instance, from the CAD data of the mask pattern by use of a CAD data checking tool 21 provided by the mask maker 2. That is, this photomask visual inspection system has the same function or effect as that of the CAD data checking tool 20 shown in FIG. 4A. Furthermore, the calculation processing for determining the offset between the origin of coordinates included in the wafer inspecting data and the origin of coordinates included in the mask inspecting data is similarly performed by the coordinate transforming computers 6. In FIG. 4B, the CAD data checking tool 21 is connected with the network 3, but in order to obtain the same function or effect, the photomask visual inspection system shown in FIG. 4B can be also arranged such that the CAD data checking tool 21 is connected with the coordinate transforming computer 6 through a dedicated line instead of the network 3.

As mentioned above, according to the embodiment 4, the photomask inspection system is arranged such that the amount of offset between the origin of coordinates included in the wafer inspecting data and the origin of coordinates included in the mask inspecting data is determined by means of calculation by use of the origin of coordinates included in the CAD data extracted by the CAD data checking tools 20 and 21. As a result, the amount of offset is automatically determined by means of causing the coordinate transforming computer 6 to perform the predetermined calculation.

What is claimed is:

1. A photomask visual inspection system that inspects a photomask by carrying out data communications with a photomask maker which produces the photomask over a network, said photomask user which processes a wafer by use of the photomask including: a wafer inspecting means for inspecting the processed wafer; and an inspection-data managing means that transmits a coordinate value which represents the position of a deficient area within a pattern located on the wafer detected by the wafer inspecting means and the wafer inspecting data used in the wafer inspecting means to said photomask maker, wherein the photomask visual inspection system has the photomask maker observe the deficient area within the photomask based on the transmitted coordinate value and wafer inspecting data.

2. A photomask visual inspection system that inspects a photomask by carrying out data communications with a photomask user which processes a wafer by way of the photomask over a network, said photomask maker which produces the photomask including:

a photomask inspecting means for inspecting the produced photomask;

a coordinate transforming means which receives a coordinate value, which represents the position of a deficient area within a pattern located on the wafer detected by a wafer inspection carried out by the photomask user, and the wafer inspecting data used in the wafer inspection, and which transforms the received coordinate value into a coordinate value which represents the position of a deficient area within a pattern located on the photomask, based on the photomask inspecting data used in said photomask inspecting means and the received wafer inspecting data; and a photomask observing means for observing the photomask, based on the coordinate value transformed by said coordinate transforming means.

3. The photomask visual inspection system according to claim 2, wherein the coordinate transforming means compares and/or collates the coordinate value, which represents the position of the deficient area within the pattern located on the photomask detected by the photomask inspecting means, with the coordinate value, which represents the position of the deficient area within the pattern located on the wafer and which is transformed into the coordinate value on the photomask, and the photomask observing means displays the results of the comparison and/or collation performed by said coordinate transforming means.

4. A photomask visual inspection system that inspects a photomask by carrying out data communications with a photomask user which processes a wafer by use of the photomask over a network, a photomask maker which produces the photomask including:

a photomask inspecting means for inspecting the produced photomask; and an inspection-data transferring means that transmits a coordinate value, which represents the position of a deficient area within the pattern located on the photomask detected by said photomask inspecting means, and the photomask inspecting data used in said photomask inspecting means to said photomask user, wherein the photomask visual inspection system has the photomask user inspect the photomask by use of the transmitted coordinate value and photomask inspecting data.

5. The photomask visual inspection system according to claim 2, wherein the coordinate transforming means determines the amount of offset with respect to the origin of coordinates included in the wafer inspecting data and the origin of coordinates included in the photomask inspecting data, and performs the coordinate transformation by incorporating the amount of offset.

6. The photomask visual inspection system according to claim 5, comprising a CAD data checking means which extracts coordinate data from the CAD data having designed the pattern located on the photomask, wherein the coordinate transforming means determines the amount of offset by use of the coordinate data extracted by the CAD data checking means.

* * * * *